United States Patent [19]

Houck

[11] Patent Number: 5,353,652

[45] Date of Patent: Oct. 11, 1994

[54] FLUID SAMPLING SYSTEM

[75] Inventor: Edward D. Houck, Idaho Falls, Id.

[73] Assignee: The United States of America as represented by the United States Department of Energy, Washington, D.C.

[21] Appl. No.: 100,952

[22] Filed: Aug. 3, 1993

[51] Int. Cl.⁵ .............................................. G01N 1/14
[52] U.S. Cl. ................................................... 73/864.34
[58] Field of Search ........... 73/863.61, 863.71, 863.81, 73/863.83, 863.85, 864.33, 864.34, 864.52, 864.73, 864.74

[56] References Cited

U.S. PATENT DOCUMENTS

| | | | |
|---|---|---|---|
| 4,118,987 | 10/1978 | Zeh | 73/863.61 |
| 4,134,289 | 1/1979 | Bohl et al. | |
| 4,638,675 | 1/1987 | Sperinck et al. | 73/864.34 |
| 5,176,035 | 1/1993 | Hartstone | 73/864.33 |

OTHER PUBLICATIONS

Spectrum '92–Nuclear and Hazardous Waste Management dated Aug. 23–27, 1992.

Primary Examiner—Robert Raevis
Attorney, Agent, or Firm—Timothy L. Harney; Hugh W. Glenn; William R. Moser

[57] ABSTRACT

An fluid sampling system allows sampling of radioactive liquid without spillage. A feed tank is connected to a liquid transfer jet powered by a pumping chamber pressurized by compressed air. The liquid is pumped upwardly into a sampling jet of a venturi design having a lumen with an inlet, an outlet, a constricted middle portion, and a port located above the constricted middle portion. The liquid is passed under pressure through the constricted portion causing its velocity to increase and its pressure to decreased, thereby preventing liquid from escaping. A septum sealing the port can be pierced by a two pointed hollow needle leading into a sample bottle also sealed by a pierceable septum affixed to one end. The bottle is evacuated by flow through the sample jet, cyclic variation in the sampler jet pressure periodically leaves the evacuated bottle with lower pressure than that of the port, thus causing solution to pass into the bottle. The remaining solution in the system is returned to the feed tank via a holding tank.

17 Claims, 3 Drawing Sheets

FLUID SAMPLING SYSTEM

CONTRACTUAL ORIGIN OF THE INVENTION

The U.S. Government has rights in this invention pursuant to Contract No. DE-AC07-84ID12435 between the Department of Energy and Westinghouse Electric Co.

BACKGROUND OF THE INVENTION

The present invention relates generally to fluidic samplers and in particular to fluid sampling in the nuclear industry.

In the nuclear industry, it is desirable to obtain unbiased samples (without dilution or concentration), without using pumps. Samples are needed to determine the chemical makeup of solutions in process vessels; without this information, the process cannot be run. Pumps are undesirable because they cannot endure high radiation fields and are therefore unreliable and maintenance intensive. Pumps also produce pressurized sample lines which represent a potential criticality danger if the sampler should leak. Pumps may be precluded on another criteria, as all existing samplers have an inherent leakage danger in a pressurized system. As a result, air lifts and/or jet ejectors with double-needle samplers or similar samplers are typically used for sampling. Another option that is used primarily in Europe and Japan is fluidic pumping of solution. However, this transfer method produces a pressurized sample line.

THEORY/OPERATION ASPECTS

The speed, reliability, and accuracy of sample systems could be improved. As analytical techniques and equipment have improved, previously undetectable sample biases and sample scattering are now being detected. The improving analytical techniques and equipment produce a developing need for unbiased samples which has increased the need for fluidic sample systems.

Presently samples are taken with jet-assisted airlift sample systems with double-needle or U-tube samplers. These systems produce samples that are biased by evaporation. While this sample bias is normally small and often insignificant (typically 0.01% to 0.10%), it is desirable to eliminate this sample bias completely to reduce the out-of-specification samples. The potential sample bias of a fluidic sample system is 0.0008% to 0.0027% from the evaporation of sample solution into the air space in the sample bottle. This is much smaller than the theoretical bias of a jet-assisted airlift sampler (0.02% to 4.0%) caused by sample evaporation of sample solution into the air space in the sample bottle. Since the degree of the theoretical or potential sample bias obtained varies from sample to sample the difficulty in obtaining replicate sample results is much higher with the jet-assisted airlift samplers with their large sample biases than with fluidic samplers with their very small sample biases.

SUMMARY OF THE INVENTION

Accordingly, it is an object of the present invention to provide a fluid sampling system that has the advantage that it does not concentrate (such as gas jet or gas lift transfers) or dilute (as do steam jets) the solution being transferred. Other fluidic sampling advantages are; very high lift capability, unbiased samples, low sample scatter, lower off-gas production with the attendant reduction in HEPA filter consumption and environmental emissions, very high dependability, and very low maintenance. A pressurized sample line requires a special sampler that is inherently safe for this enriched uranium solution sampling application to be safe. In this application the sampler must leak into the sample line to prevent an inadvertent transfer of solution to the sample cubicle. The fluidic sampler of the present invention provides the required leaking into the sample line characteristic to prevent the inadvertent transfer of solution into the sample cubicle.

A fluid transfer system is disclosed which is used to pump solution out of a pumping chamber through a venturi valve ejector, entraining solution from a feed tank and transferring the combined solution streams to a fluidic sampler. Jets use the venturi principle to entrain solution from the feed tank so more solution is pumped out of the jet than is fed to the jet inlet. In a fluidic application, this greatly increases the pumping rate of the jet. The pumping chamber is filled with air, which forces solution out of the chamber. The pressurized air is turned off and vented through an orifice vent line, which allows the pumping chamber to be refilled with solution from the feed tank. Since the air used to pump solution from the pumping chamber does not pass through the jet, the fluidic systems essentially uses the solution to be transferred to pump itself. From the fluidic sampler, fluid is transferred to a return carboy, where it is accumulated for return to the feed tank.

The fluidic sampler uses the venturi principle to prevent escape of fluid from the system. By constricting the size of the lumen through the sampling jet, pressure is reduced in an adjacent port. In order to take samples, a sample bottle having a hollow needle extending therefrom is used to pierce a septum over the port permitting the fluidic sampler to evacuate the sample bottle. As the sampling jet pressure varies cyclically, the evacuated bottle's pressure is periodical lower than the sampling jet pressure. When this occurs, the evacuated bottle draws fluid into it, after which the needle and bottle may be removed.

Since the sampler inlet line to the fluidic sampler system is pressurized, the fluidic sampler must be designed such that air and solution enter the sampler from the sample cubicle, but do not exit the sampler into the sample cubicle. This sampler characteristic is required to minimize the criticality danger in the sample cubicle caused by the potential of spilled uranium bearing solutions. The present fluidic jet sampler meets this criterion by geometry. The feed port is under vacuum whenever solution is being transferred, so that no solution can leave the sampler into the sample cubicle. A septum in the inlet port of the jet sampler provides a seal to prevent solution transfer into the sample cubicle and provides the means to sample the solution. The fluidic sampler is safe, since the fluid flow path is naturally into the fluidic sampler while the natural fluid flow path is out of the existing sampler designs.

BRIEF DESCRIPTION OF THE DRAWINGS

The present invention is illustrated in the accompanying drawings wherein.

DETAILED DESCRIPTION OF THE PREFERRED EMBODIMENT

Figure 1:
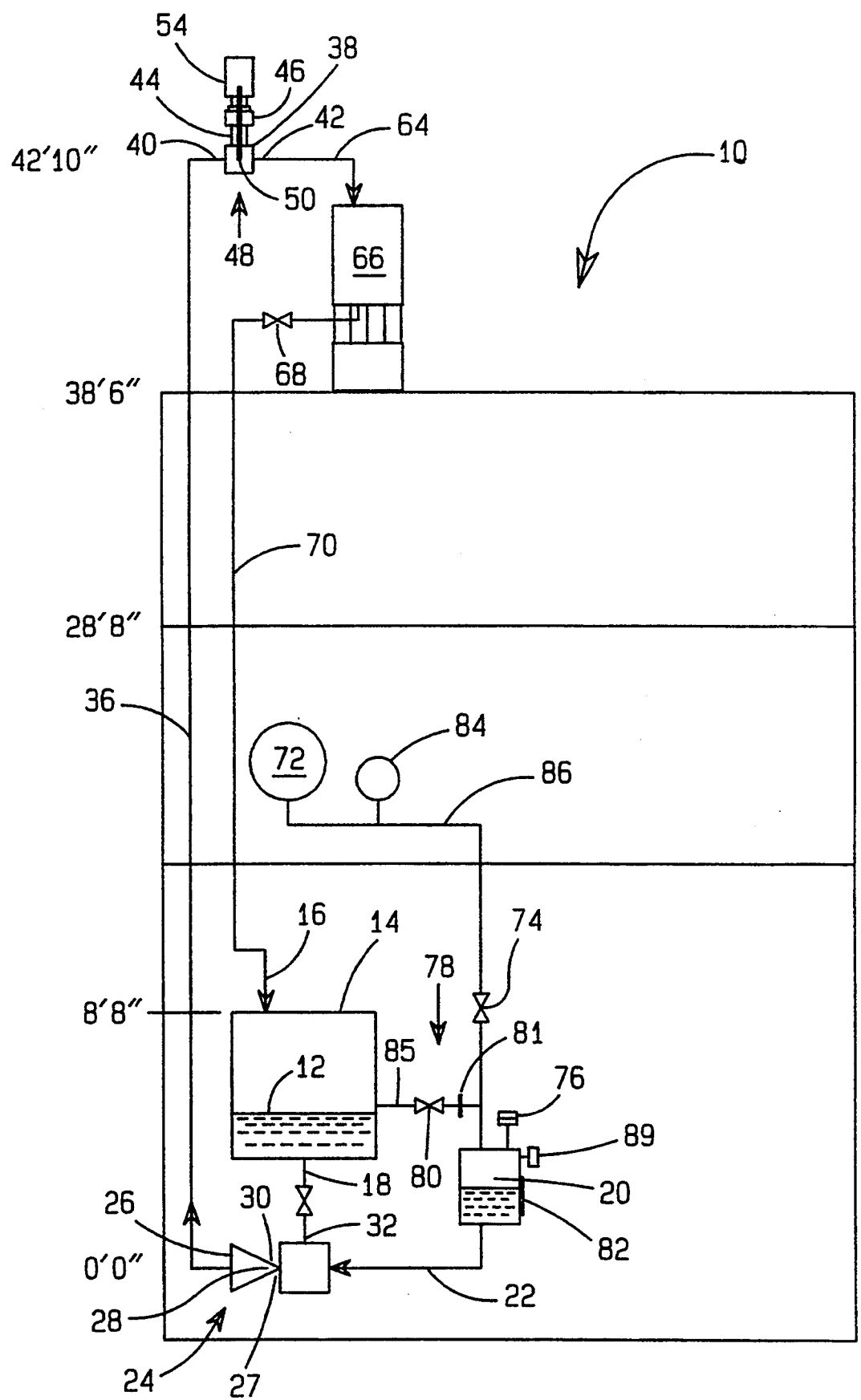
FIG. 1 is a schematic diagram of a fluid sampling system.

As shown in FIG. 1 of the drawings, a substantially sealed system 10 for sampling fluid 12 is shown. System 10 includes a feed tank 14 for the storage of fluid 12. Feed tank 14 has an inlet 16 and outlet 18 for the ingress and egress of fluid 12. A pumping chamber 20 is used for pumping fluid 12 from the feed tank 14 and through system 10. In the embodiment shown pumping chamber 20 is located below feed tank 14. Pumping chamber 20 is in fluid communication with feed tank 14. Pumping chamber 20 is connected to and in fluid communication with system 10 for pumping fluid 12 through system 10. By this it is meant that system 10 has a series of elements which are interconnected by tubing for carrying fluid 12 therethrough. Fluid 12 is pumped through system 10 by means of pumping chamber 20. In one embodiment, tubing 22 preferably comprises ¾" flexible polyethylene tubing. However, stainless steel tubing and stainless steel elements of system 10 are preferred when radioactive material is being used.

A transfer jet 24 is provided for selectively allowing the flow of fluid 12 through system 10. In the embodiment shown, transfer jet 24 allows the passage of fluid 12 from pumping chamber 20 through the remainder of the system 10. In the embodiment shown, transfer jet 24 includes a venturi nozzle 26 which causes fluid to be drawn directly from feed tank 14 into transfer jet 24. This is accomplished by having venturi flow through a central lumen 28 having a constricted portion 30 (metal nozzle) and a port 32 located above constricted portion 30 which is connected to feed tank 14. As a result, when pumping chamber 20 is filled with fluid 12 and is actuated, the flow of fluid 12 through transfer jet 24 creates a vacuum in port 32 thereby drawing fluid 12 from feed tank 14 into transfer jet 24. Thus, fluid 12 from both pumping chamber 20 and feed tank 14 passes out of transfer jet 24 through tubing 36. In the preferred embodiments tubing 36 extends vertically to well above a feed tank 14. By way of example and as shown in FIG. 1, feed tank 14 has a top that is located 8 feet 8 inches from ground level. Tubing 36 extends to a height of 42 feet 10 inches. At the top of the system 10, tubing 36 is directed horizontally and into a fluidic sampler 38.

Figure 2:
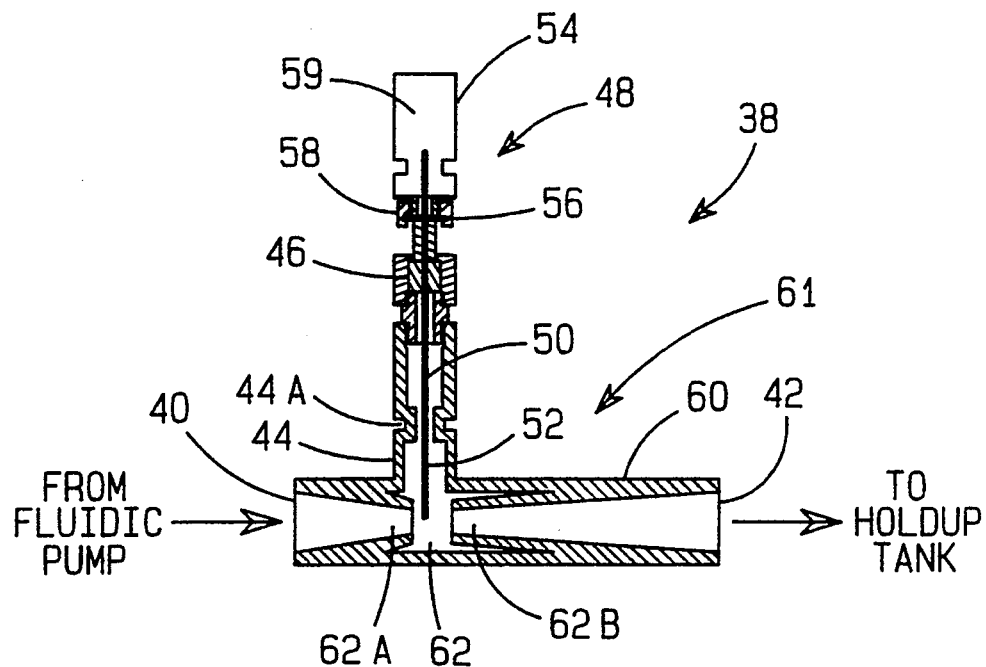
FIG. 2 is an elevation view of a sampling jet with a sample bottle in place.

As shown in FIG. 2, fluidic sampler 38 has an inlet 40, an outlet 42 and a port 44 sealed with a pierceable flexible septum 46. Port 44 also may have a constricted middle portion 44A to further reduce the likelihood of inadvertent spillage. Although in the embodiment shown in FIG. 2, a septum is used for sealing port 44, other sealing means such as that shown in FIG. 4 may be used for selectively sealing port 44 and for alternatively drawing samples therefrom. Fluidic sampler 38 is in fluid communication with transfer jet 24 and feed tank 14 by means of tubing 36 and 70.

As is further shown in FIG. 2, a mechanism 48 for piercing pierceable septum 46 is provided. Mechanism 48 is used for withdrawing a desired quantity of fluid 12 from system 10. In the embodiment shown the mechanism 48 for piercing septum 46 is a hollow needle 50 having lumen 52 extending therethrough. Hollow needle 50 extends through septum 46. Mechanism 48 further comprises a bottle 54 having a bottle septum 56 sealing its end 58. In a preferred embodiment, sample bottle 54 is either a conventional 5 ml or 15 ml liter glass bottle. Needle 50 extends through bottle closure 56 and into the interior 59 of a bottle 54. Alternatively, mechanism 48 for piercing septum 46 may comprise a conventional syringe, (not shown in the drawings).

Sampling jet 61 may be generally described as horizontal tube 60 in fluid communication with inlet 40 and outlet 42. A constricted middle portion 62 of tube 60 constricts the flow of fluid therethrough. Constricted middle portion 62 has two opposing nozzles 62A and 62B of decreased diameter. As a result, the velocity of fluid 12 going through tube 60 increases but the pressure within a port 44 located above and in fluid communication with constricted portion 62 is reduced. This reduction in pressure prevents fluid 12 from escaping through port 44. This prevents dispersion of radioactive material in cases where fluid 12 is radioactive. After fluid 12 passes out of outlet 42, it is carried by means of tubing 64 to return holding tank 66 where it is accumulated and released by valve 68 into tubing 70 downwardly into feed tank 14. Holding tank 66 is located slightly below fluidic sampler 38 in order to create additional gravity feed from outlet 42. Thus, a closed system is created in which the fluid 12 is circulated, and sampled, as required.

Although a wide variety of pumping mechanisms may be utilized, in the embodiment shown in FIG. 1, an air compressor 72 is utilized to send compressed air to pumping chamber 20. In operation, fluid 12 is gravity fed into pumping chamber 20 until it is full. Compressor 72 then sends compressed air through valve 74, forcing fluid 12 out of pumping chamber 20 and into transfer jet 24. In a preferred embodiment, compressor 72 pumps compressed air at a pressure of approximately 170 pounds per square inch. Fluid 12 is pumped at an average rate of 0.02 to 0.05 gals./min. (77–192 cc/minute). A Fox brand Liquid-Liquid jet used in transfer jet 24 produces a peak vacuum at 75 pounds per square inch gauge motive air while A Penberthy brand jet produces a peak vacuum with only 32 pounds per square inch gauge motive air. Accordingly, the Fox Liquid-Liquid Jet is preferred in transfer jet 24 to permit operation at the higher pressure.

In operation, pumping chamber 20 is filled and emptied several times before a sample is taken. Air is vented out of pumping chamber 20 by means of vent valve 80 as fluid 12 is gravity fed into the pumping chamber via outlet 18, port 32 and tubing 22. A pressure relief valve 76 prevents the over pressurization of the pumping chamber during the pumping step.

Also illustrated in FIG. 1 is a control mechanism 78 for controlling the pumping of fluid 12 from pumping chamber 20. The control mechanism 78 empties pumping chamber 20 to a desired level and then vents air from the chamber. The control mechanism 78 includes valve 74 for controlling the passage Of compressed air into chamber 20, vent valve 80 between feed tank 14 and pumping chamber 20, and a fluid level sensor 82 in pumping chamber 20. When fluid 12 in pumping chamber 20 reaches a low level, valves 74 and 80 are operated to cut off the flow of compressed air from compressor 72 and permit passage of fluid 12 from feed tank 14 into the pumping chamber 20 via outlet 18, port 32 and tubing 22.

Another means for controlling the flow of fluid 12 using control mechanism 78 is by use of a flow sensor 84 in air line 86. Flow sensor 84 measures the flow of air into pumping chamber 20. By registering rapid changes in air flow, flow sensor 84 indicates when pumping chamber 20 is empty. Valves 80 and 74 may then be operated in order to stop the flow of air, shut off compressor 72 and begin refilling pumping chamber 20 with fluid 12.

One other manner of controlling the pumping of fluid 12 in conjunction with transfer jet 24, pumping chamber 20 and feed tank 14 is described in U.S. patent application Ser. No. (DOE Docket No. S-76,774) filed May 27, 1993 by Edward D. Houck, entitled Vortex Diode Jet, assigned to the U.S. Department of Energy. This application is hereby incorporated by reference for this purpose.

Fluid 12 discharged from transfer jet 24 passes through tubing 36 to fluidic sampler 38 where the fluid is available for sampling. In order for fluid 12 to flow through hollow needle 50 into sample bottle 54, the pressure within the interior of sample bottle 54 must be lower than that of the pressure within port 44. The fluidic sampler sample jet first evacuates the sample bottle through the needle 50. Then the periodic pressure variations of the sample jet cyclically provides the lower bottle pressure required for sampling. In a preferred embodiment, sample bottle 54 is 20 milliliters in interior size in order to receive samples of 15 milliliters of fluid 12.

Figure 3:
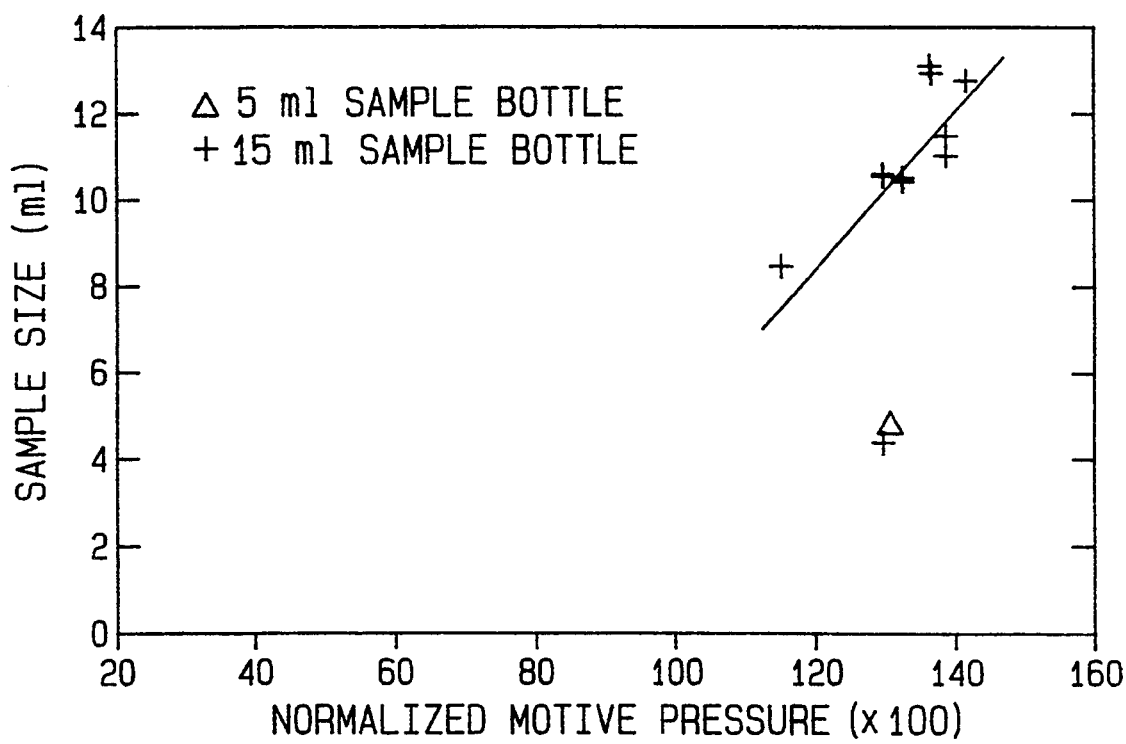
FIG. 3 is a chart showing sample size relative to the normalized motive pressure in the sampling system of FIG. 1.

FIG. 3 shows a chart comparing 5 milliliter and 15 milliliter sample bottles and actual peak motive pressure in relationship to the sample size. The sample size increases with higher motive pressure. Obviously, the sample size is also dependent on the sample bottle size.

Figure 4:
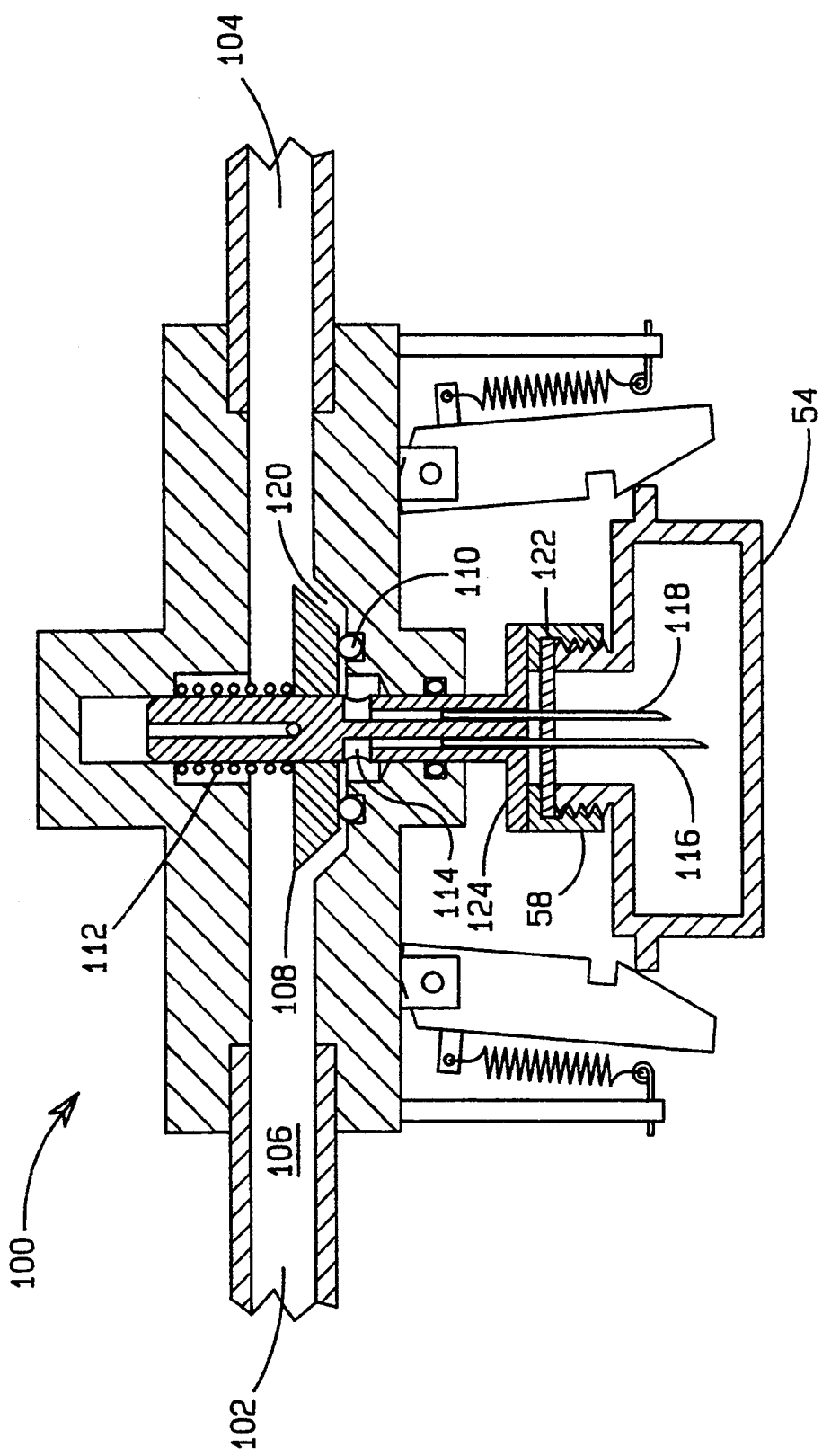
FIG. 4 is a side cut-away view of an alternative sampling valve.

FIG. 4 of the drawings illustrates an alternative sampling device 100 having an inlet 102, an outlet 104 and a lumen 106 extending therethrough. A constricting member 108 is positioned in the middle of lumen 106. In this embodiment, rubber O-ring 110 seals the constricting member 108 at its bottom portion. A spring 112 is positioned to bias constricting member 108 against O-ring 110 and thereby seal both the opening and discharge of a passageway 114. In order to open passageway 114, a sample bottle 54 is pressed upwardly against a plunger 124 which in turn presses against constricting member 108 thereby lifting it from O-rings 110 and allowing the passage of fluid 12 into sample bottle 54. Sample bottle 54 includes a cap 58 retaining a septum 122 which is penetrated by hollow needles 116 and 118 in fluid flow communication with the opening and discharge portions of passageway 114.

In operating the fluid sampling system 10, the inventor has found little or no difference in pumping rates between pumping until air just starts to flow through venturi 26 (blowout) and pumping until just before the air flows through the venturi 26 (no blowout). When air pressure is released through venturi 26, the fluidic pump system 10 can be controlled and cycled by a pressure switch 89. The pressure drop, which occurs with blowout through venturi 26, is essentially instantaneous and significant, typically a pressure drop in the pumping chamber of 10-20 psi.

When controlling the pumping chamber 20 level so that air does not pass through the venturi 26, (no "blowout" operation) the liquid level in pumping chamber 20 can be monitored by level probe 82 and the system cycled just before chamber 20 is emptied.

No blowout operation also can be performed by determining air flow time required to empty pumping chamber 20. The time to empty the pumping chamber 20 is a simple relationship between the air pressure, the pumping chamber 20 size, the orifice sizes 27 and 30 of the venturi 26, the solution density and the feed tank level. Fixing the motive air pressure, the pumping chamber 20 size, and the orifice size essentially frees the pumping time as the feed tank 20 level and the solution density effects are fairly small. A few simple tests will establish the 85-95% evacuation of the pumping chamber 20 evacuation time for the range of solution densities and feed tank 14 levels that the system would see. A simple timer may also be used to open and close the motive air inlet valve. Either the blowout or the no blowout operating systems can be easily controlled by a timer. The no blowout operating system can also be tied into a computer that would vary the pumping time by factoring in the effects of pumping air pressure, solution density, solution viscosity, and the level of solution in the feed vessel 14.

Either control system can be adapted for reliable use; the no blowout system is preferred for sampling work since it would produce zero solution evaporation.

The pumping rate is nonlinearly related to the pumping pressure. As the motive air supply is opened, the pressure in the pumping chamber 20 increases to the maximum of the source pressure minus the inlet line pressure losses. Until the maximum pumping pressure is reached, the pumping rate is less than the maximum for the particular motive pressure. Pumping out a full pumping chamber 20 until it is empty or almost empty minimizes the time until the maximum pumping rate is achieved and maximizes the duration of the maximum pumping rate. Pumping the pumping chamber 20 from full to empty maximizes the overall pumping rate for a particular motive pressure.

EXPERIMENTAL DESCRIPTION

A major advantage of fluidic transfer and fluidic sampler systems is their ease of operation. The sampling system 10 was operated two different ways with each way using two different methods of control for controlling the pumping cycle duration and the pumping chamber 20 refill duration. The first method of operation was the use of an orifice 81 in the pumping chamber 20 vent line 85. The steps to operate fluid sampling system 10 with an orifice 81 in the pumping chamber 20 vent line were as follows:

1. The first step was opening the air inlet valve 74 to the pumping chamber 20.
2. The air inlet valve 74 was then closed when the proper control criteria was met. The two control criteria for the pumping chamber 20 level being down to the desired level were; sight glass level indication of the desired pumping chamber 20 operating level (partially empty to empty pumping chamber 20, no blowout operation) and pumping chamber 20 pressure drop (empty pumping chamber 20, blowout operation).
3. Pumping chamber 20 refill. The start of the next pumping cycle was delayed until the pumping chamber 20 refilled with solution 12 from the feed tank 14. The refill step duration was controlled by pumping chamber 20 level indication or by timing the duration of the refill.
4. Repeat steps 1-3 as desired for additional pumping cycles.

The second method of operation was the use of a shut-off valve 80 in the pumping chamber 20 vent line 85. The steps to operate a fluidic transfer system 10 with a shut-off valve 80 in the pumping chamber 20 vent line 85 were as follows:
1. The shut-off valve 80 was closed.
2. The air inlet valve 74 was opened to pumping chamber 20.
3. The vent line shut-off valve 80 was then opened when the proper control criteria was met. The two control criteria for the pumping chamber 20 level being down to the desired level were; sight glass level indication for the desired pumping chamber 20 level (partially empty to empty pumping chamber 20, no blowout operation) and pumping chamber 20 pressure drop (empty pumping chamber 20, blowout operation).
4. The pumping chamber 20 air inlet valve 74 was closed immediately after the vent line shut-off valve 80 was opened. Opening the shut-off valve 80 first maximizes the possible duration of the high pressure pumping cycle regime.
5. Pumping chamber 20 refill. The start of the next pumping cycle was delayed until the pumping chamber 20 refilled with solution 12 from the feed tank 14. The refill step duration was controlled by pumping chamber 20 level indication or by timing the duration of the refill.
6. Repeat steps 1-5 as desired for additional pumping cycles Once the fluidic sampler 38, the pumping chamber 20 and the sample lines 36, 64, 70 and 86 have been flushed with solution 12 from the feed tank 14, typically three pumping cycles of the pumping chamber 20, accountability quality samples can be taken. A sample can be taken any time during the pumping cycle once the system 10 has been flushed. The easiest and best method is to place the sample needle 50 and sample bottle 54 in place on the fluidic sampler 38 prior to starting the pumping cycle.

When a sample needle 50 and bottle 54 are in place on the sampler septum 56, the sample bottle 54 is evacuated during the pumping cycle, and the bottle 54 fills with sample solution 12 during the pumping cycle and the pumping chamber 20 refill cycle. No solution transfer can take place without the sample needle 50 and the sample bottle 54 in place. Once the sample bottle 54 is filled, it can be removed from the sample needles 50 and another bottle 54 placed on the sample needle for additional samples.

RESULTS

The fluid sampling system 10 operated easily and dependably. System 10 with a fluidic sampler 38 in-line transferred water to a net lift of 37.2-39.9 feet at an acceptable average rate of 0.02-0.05 gpm (77-192 cc/min).

The sample size taken by the fluidic sampler 38 is dependent on the motive pressure and the characteristics of the constriction 62 in fluidic sampler 38. The inventor has found that a one half-inch Fox Liquid-Liquid Jet produces a peak vacuum with about 75 psig motive fluid while a one half-inch A Penberthy GL Jet produces a peak vacuum with about 32 psig motive fluid. As shown in FIG. 3, the higher the normalized motive pressure (actual motive pressure/peak vacuum motive pressure), the larger the sample. Further, as shown in FIG. 3, the sample size is dependent on the sample bottle size 54. However, the percent of the sample bottle 54 filled is dependent only on the normalized fluidic sampler 38 motive pressure (and on the fluidic sampler jet 61 characteristics). Therefore, any sample size is obtainable with a fluidic sampler 38 with the use of the correct size sample bottle 54. The fluidic sampler 38 achieved an acceptable flow rate and supplied samples of an adequate size (approximately 10 ml) without leakage from the sampler.

To obtain adequate sized samples (>10 ml in 15 ml sample bottles) 140-150 percent of the peak motive pressure for the constriction in the fluidic sampler 38 was required. At higher motive pressure the jet is acting in an inductive mode. While the sampler is not in the inductive mode sample solution did not enter the fluidic sampler port 44 section where it could be sampled. Only with a significant over peak vacuum motive pressure, does the motive fluid stream overwhelm the constriction 62 and force liquid into the port 44. Only when sample solution is being forced into and circulated through the port 44 are adequately sized, unbiased samples obtainable. Slightly larger samples (12-13 ml versus 11-11.5 ml in 15 ml sample bottles) where obtained at 150 percent normalized motive pressure with needles that extended to the bottom of the sampler.

The fluidic samplers have high resistive flow coefficients ($K=18,000$ for the Fox fluidic sampler, and $K=59,000$ for the Penberthy fluidic sampler). The high resistive flow coefficients for the fluidic samplers means that the motive air source for the pumping chamber 20 must be properly sized to deliver the motive pressure required at the fluidic samplers jet 61.

The portion of the pumping chamber 20 evacuated during the high pressure part of the pumping cycle is important. The higher the percentage of the pumping chamber 20 evacuated, the longer the high pressure, high flow rate section of the pumping cycle. If the pumping air is turned off too soon then more of the pumping cycle will be used with low-pressure, low-flow rate pumping. Pumping until the air almost or just begins to bubble through the jet insures the maximum pumping pressure over the longest possible period and the maximum average pumping rate. Likewise, starting the pumping cycle before the pumping chamber 20 completely refills reduces the average pumping rate.

The volume of the sample taken with a fluidic sampler 38 is dependent on the motive pressure to the fluidic sampler 38, the sample bottle size 54, and on the characteristics of the fluidic sampler jet 61. The fluidic sampler 38 should have its motive pressure at 140-150 percent of that required for the peak vacuum pull. Needles 50 that go to the bottom of the port 44 should be used when maximum sample size is required.

Out-of-specification samples may be reduced by approximately 50% by using a fluidic sample system. As the analytical methods improve, the variability and the bias a jet-assisted airlift sampler produces will prevent samples from passing acceptable standards of replication. The increase in sample quality and a small decrease in sampling time produced by a fluidic sample system will be economically beneficial by reducing operation time and analytical time, and reducing the amount of wasted supplies and chemicals.

Fluidic sample systems can be used beneficially where pumps are not practical and where it is important not to change the sample concentration. Fluidic sample systems have the advantage over jet-assisted airlift sample systems in that they do not evaporate the solution and require very little submergence to sample a tank. They can also perform transfers in one stage, whereas two or three stages of jet-assisted airlift sampler systems would be required.

The foregoing description and drawings merely explain and illustrate the invention, and the invention is not limited thereto except insofar as those who have the disclosure before them are able to make modification and variations therein without departing from the scope of the invention.

The embodiment of the invention in which an exclusive property or privilege is claimed is defined as follows:

1. A substantially sealed system for sampling a fluid comprising:
   a feed tank for the storage of said fluid to be sampled;
   a pumping chamber in fluid communication with and located at least partially lower than said feed tank;
   said pumping chamber being connected to and in fluid communication with said system for pumping said fluid through said system;
   transfer jet means in fluid communication with said chamber and said feed tank for selectively allowing the flow of said fluid through said system, said transfer jet means including a venturi nozzle;
   cyclic control means for alternately expelling said fluid from said pumping chamber and permitting said chamber to refill with fluid through said venturi nozzle;
   means for pressurizing said system for expelling fluid from said pumping chamber through said transfer jet means;
   venting means for venting air from said pumping chamber as said pumping chamber is refilled;
   a fluidic sampler jet having an inlet, an outlet, a port having selectable sealing means, said fluidic sampler being in fluid communication with said pumping chamber and located substantially above said feed tank;
   means for piercing said sealing means of said fluidic sampler jet and withdrawing a portion of said fluid as a sample; and
   means connected to the outlet of said fluidic sampler for returning the remainder of said fluid to said feed tank.

2. The system of claim 1 wherein said means for piercing said sealing means and withdrawing a sample comprises a syringe.

3. The system of claim 1 wherein said sealing means comprises a piercable flexible septum and wherein said means for piercing said sealing means and withdrawing a sample comprises;
   a sample bottle;
   a hollow needle having a first end portion in fluid communication with said sample bottle and a second end portion capable of penetrating said septum and withdrawing a sample into said sample bottle.

4. The system of claim 3 wherein said sample bottle having a bottle closure sealing a first end thereof, said needle being disposed through said bottle closure and into said bottle.

5. The system of claim 1 wherein said sealing means comprises a pierceable septum.

6. The system of claim 1 wherein said feed tank, said pumping chamber, said transport jet means and said fluidic sampler jet are connected by tubing, and a holding tank is located below said fluidic sampler and in fluid communication therewith for receiving said fluid from said fluidic sampler.

7. The system of claim 1 wherein said means for pressurizing said system comprises an air compressor in fluid communication with said pumping chamber.

8. The system of claim 1 wherein fluidic sampler jet comprises;
   a horizontal tube in fluid communication with said inlet and said outlet;
   a constricted portion of said tube, and a port located above said constricted portion of said tube, said constricted portion being effective to increase the velocity of flow of said fluid through said constricted portion and to reduce the pressure within said port thereby preventing said fluid from escaping from said port.

9. The system of claim 1 whereby said pumping chamber further includes,
   control means for pumping said fluid from said pumping chamber until said pumping chamber is emptied to a desired level;
   venting means for venting air from said pumping chamber as said pumping chamber is refilled.

10. The system of claim 1 wherein said control means comprises a fluid level sensor in said pumping chamber.

11. The system of claim 1 wherein said control means comprises an air flow sensor for measuring air flow into said pumping chamber, said air flow sensor being effective to indicate when said pumping chamber is empty.

12. A sampling device for a pressurized fluid pumping system, said device comprising;
   a sample jet adapted for connection to, and in fluid communication with said system;
   said sample jet having an inlet, an outlet, a lumen extending longitudinally therethrough, a constricted middle portion of said lumen and a port extending into said lumen adjacent said constricted middle portion, whereby fluid may be sampled from said port without being dispersed out of said port into the atmosphere;
   a piercable septum sealing said port, a sealed sample bottle, and a hollow needle having a first end portion in fluid communication with said sample bottle; and
   said septum being constrained and arranged for piercing by a second end portion of said hollow needle so as to allow said fluid to flow into said sample bottle.

13. The sampling device of claim 12 wherein said sample bottle is evacuated to a lower pressure than said port during flow of said fluid through said sample jet so as to draw said fluid into said bottle.

14. The system of claim 12 wherein said sample jet compresses a half-inch lumen beginning at said inlet and said outlet and extending substantially through said jet.

15. The system of claim 12 wherein said sample bottle is between 5 ml. and 15 ml. in internal volume.

16. A substantially sealed system for sampling a fluid comprising:
   a feed tank for the storage of said fluid to be sampled;
   a pumping chamber in fluid communication with and located at least partially lower than said feed tank;
   said pumping chamber being connected to and in fluid communication with said system for pumping said fluid through said system;
   a venturi nozzle located below said feed tank and in fluid communication for selectively allowing the flow of said fluid through said system, said venturi nozzle having an inlet, an outlet, a lumen extending therethrough, a port in fluid communication with said feed tank, and a constricted middle portion within said lumen and connected to said port, said inlet being in fluid communication with said pumping chamber so that fluid pumped from said pumping chamber flows through said lumen thereby creating a vacuum in said port, said vacuum being effective to draw said fluid from said feed tank whereby fluid may be pumped through said system free of air;

means for pressurizing said system;

a fluidic sampler jet having an inlet, an outlet, a port having selectable sealing means, said fluidic sampler being in fluid communication with said pumping chamber and located substantially above said feed tank;

means for piercing said sealing means of said fluidic sampler jet and withdrawing a portion of said fluid as a sample; and means connected to the outlet of said fluidic sampler for returning the remainder of said fluid to said feed tank.

17. The system of claim 16 further comprising;

cyclic control means for alternately expelling said fluid from said pumping chamber and permitting said chamber to refill with fluid through said venturi nozzle; and venting means for venting air from said pumping chamber as said pumping chamber is refilled.

* * * * *